(12) United States Patent
Josephson et al.

(10) Patent No.: US 7,732,408 B2
(45) Date of Patent: Jun. 8, 2010

(54) REPRODUCTIVE MANAGEMENT

(75) Inventors: Scott Josephson, Taunton, MN (US);
Bruce James Iverson, Garvin, MN (US); Rodney A. Schulze, Holland, MN (US)

(73) Assignee: IverSync II LLC, Holland, MN (US)

( * ) Notice: Subject to any disclaimer, the term of this patent is extended or adjusted under 35 U.S.C. 154(b) by 726 days.

(21) Appl. No.: 11/584,010

(22) Filed: Oct. 19, 2006

(65) Prior Publication Data

US 2007/0123461 A1 May 31, 2007

Related U.S. Application Data

(60) Provisional application No. 60/728,076, filed on Oct. 19, 2005.

(51) Int. Cl.
*A61K 38/00* (2006.01)
*A61K 31/56* (2006.01)

(52) U.S. Cl. .................................. 514/12; 514/177

(58) Field of Classification Search ............... None
See application file for complete search history.

(56) References Cited

U.S. PATENT DOCUMENTS

| | | | |
|---|---|---|---|
| 4,089,951 A | 5/1978 | Fur | |
| 5,589,457 A | 12/1996 | Wiltbank et al. | |
| 6,423,039 B1 * | 7/2002 | Rathbone et al. | 604/286 |
| 7,208,265 B1 * | 4/2007 | Schenk | 435/1.1 |
| 2003/0059951 A1 | 3/2003 | Frushour et al. | |

OTHER PUBLICATIONS

Pfizer Animal Health, Dairy Overview for CIDR, Internet Page, printed on Jul. 25, 2007, http://www.cidr.com/product_overview.asp?country=US&lang=EN&species=DA&drug=CI.
Pfizer Animal Health, Dairy Detail for CIDR, Internet Page, printed on Jul. 26, 2007, http://www.cidr.com/product_detail.asp?country=US&lang=EN&species=DA&drug=CI.
DEC International, Product Information for CIDR, Drug Information Sheet, available at http://www.cidr.com/PAHimages/compliance_pdfs/US_EN_CI_compliance.pdf.
Pharmacia & Upjohn, Material Safety Data Sheet for CIDR, Apr. 4, 2002, available at http://www.cidr.com/PAHimages/msds_us/Cl.pdf.
Pfizer Animal Health, Answers to Frequently Asked Questions about CIDR, Internet Page, printed on Jul. 25, 2007, http://www.cidr.com/QandA.asp?country=US&lang=EN&species=DA&drug=CI.
Pfizer Animal Health, Dairy Overview for Lutalyse, Internet Page, printed on Jul. 25, 2007, http://www.lutalyse.com/product_detail.asp?country=US&lang=EN&species=DA&drug=LT.
Pfizer Animal Health, Dairy Detail for Lutalyse, Internet Page, printed on Jul. 25, 2007, http://www.lutalyse.com/product_detail.asp?country=US&lang=EN&species=DA&drug=LT.
Pharmacia & Upjohn, Product Information for Lutalyse, Drug Information Sheet, Jun. 2004, available at http://www.lutalyse.com/PAHimages/compliance_pdfs/US_EN_LT_compliance.pdf.
Pharmacia & Upjohn, Material Safety Data Sheet for Lutalyse, Jun. 23, 1997, available at http://www.lutalyse.com/pahimages/msds_us/Lutalyse.pdf.
Pfizer Animal Health, Answers to Frequently Asked Questions about Lutalyse, Internet Page, printed on Jul. 25, 2007 http://www.lutalyse.com/QandA.asp?country=US&lang=EN&species=Da&drug=LT.
Fricke, Paul M., Reproductive Management of Dairy Heifers, available at http://www.wisc.edu/dysci/uwex/rep_phys/pubs/heifers502.pdf.
Cordoba, M. C., Sartori, R., & Fricke, P. M., Assessment of a Commercially Available Early Conception Factor (ECF) Test for Determining Pregnancy Status of Dairy Cattle, J. Dairy Sci., Aug. 2001 84(8):1884-9.
Merial, Product Information for Cystorelin, Drug Information Sheet, available at http://merialusa.naccvp.com/view.php-?prodnum=1111008.
Merial, General Information for Cystorelin, Internet Page, printed on Jul. 26, 2007, http://us.merial.com/producers/dairy/products_cystorelin.asp#.
Schering-Plough Animal Health, Drug Information Sheet for Estrumate, available at http://www.mycattle.com/estrumate/S517-005310_EST_50dose_SS_04.pdf.
EDP Biotech Corp., General Information for EDP/ECF, Internet page, printed on Jul. 26, 2007, http://edpbiotech.com/our_products/veterinarian_diagnostics/cow_testing/cow_testing.html.
EDP Biotech Corp., EDP/ECF Frequently Asked Questions, Internet page, printed on Jul. 26, 2007, http://edpbiotech.com/our_products/veterinarian_diagnostics/cow_testing/faqs/faqs.html.
International Search Report for PCT/US06/40832, dated Mar. 28, 2008.
Written Opinion of the International Searching Authority; PCT Application No. PCT/US06/40832; dated Mar. 25, 2009.

* cited by examiner

*Primary Examiner*—Shanon A Foley
(74) *Attorney, Agent, or Firm*—Patterson Thuente Christensen & Pedersen, P.A.

(57) ABSTRACT

A method for breeding, especially a method for breeding dairy cattle without use of heat detection prior to insemination.

19 Claims, No Drawings

REPRODUCTIVE MANAGEMENT

The present application claims the benefit of U.S. Provisional Application No. 60/728,076 filed Oct. 19, 2005, which is incorporated herein in its entirety by reference.

FIELD OF THE INVENTION

The invention is directed toward breeding methods for bovines, particularly dairy cattle, including lactating dairy cattle.

BACKGROUND OF THE INVENTION

Dairy cattle operations require efficient breeding regimens for optimal performance and economic yield. Milk production is dependent on cows in the operation becoming pregnant, giving birth and lactating. After birth a cow can be milked for over two hundred days. However, after about 150 days post parturition, the amount of milk produced begins to fall off rapidly. Thus, minimizing the period of time between calving and the beginning of the next pregnancy increases the value of the cow to the dairy operation.

Moreover, the economic value to a dairy operation of a typical cow decreases rapidly thirty six months after first calving. Increasing the number of pregnancies that a cow has during this time maximizes the return on investment in the animal in terms of feed, overhead and other costs.

In recent years, several hormone products have come on the market for manipulation of the estrus cycle in cows. These products include gonadotropin releasing hormone (GnRH), lutenizing hormone LH, prostaglandin F2α, estrogen, progesterone and synthetic analogs of certain of these hormone. Each of these products are used at various times in the estrus cycle to encourage ovulation or otherwise aid in conception and maintenance of pregnancy.

Progesterone levels may elevated in cows by use of exogenously applied progesterone and used, for example, to synchronize estrus in a herd. Application or treatment is conveniently done using a vaginal insert that is constructed to release progesterone at a steady rate. The EAZI-BREED™ CIDR® is produced by DEC International, NZ Ltd. and available in the U.S. from Pfizer Animal Health Products (New York, N.Y.). The CIDR insert is indicated for protocols that allow for synchronization of the a cow's estrus cycle thereby giving the dairy cattle operation a better chance of detecting heat in the cows by narrowing the window in which to place the cow under increased scrutiny. Indeed, the protocols for which the CIDR insert are approved require heat detection to determine optimal time for artificial insemination. For example, in the FAST BACK$^{SM}$ method for lactating dairy cows, a cow undergoes artificial insemination and a CIDR insert is administered fourteen days later. At Day 21, the CIDR is removed and the animal is observed over Days 22-25 for heat detection and inseminated on observation of heat. However, use of prostaglandins (such a LUTALYSE®) are contraindicated in this protocol.

Unfortunately, heat detection is difficult, requires proper training and experience to do correctly and is time consuming for the operator and employees in a dairy operation. Some authorities recommend observation of the animals at least three times daily. Certain signs of heat, such as standing heat, may only be present for ten hours within a single estrus cycle. Many signs of heat are also subtle and easy to miss. Large dairy operations often employ many unskilled workers who do not have the necessary training to carry out heat detection. Some estimates place failure of heat detection at or higher than 50%. Missing an observed heat means another estrus cycle must occur before breeding can be attempted again.

Some methods, such as the Ovsynch method have proposed estrus cycle modification using certain hormone injection regimens and the elimination of heat detection. However, at least one evaluation of the Ovsynch method has shown that the method does not give acceptable rates of conception using a fixed-time artificial insemination without heat detection. See, e.g., "Reproductive Management of Dairy Heifers" by Paul M. Fricke, Ph.D. of the Department of Dairy Science, University of Wisconsin-Madison.

Thus, a method is needed to ensure increased breeding efficiency with reduction in the number of months in the breeding cycle without the need for heat detection prior to breeding.

SUMMARY OF THE INVENTION

According to one aspect of the invention, dairy cows are inseminated at a suitable time after maturation or parturition, progesterone is administered nineteen days after insemination, ultrasound is performed on the cow twenty six days after insemination a determination is made whether the cow is open. Ultrasound may be performed no later than twenty seven or twenty six days after insemination. Progesterone may administered to the cow nine days before insemination by application of a vaginal insert or other route. Where a vaginal insert is used for administration, the insert is removed two days before insemination. Gonadotropin releasing hormone may also be administered to the cow nine days before insemination. Prostaglandin F2α or cloprostentol may also be administered to the cow two days before insemination. If the cow is open after insemination, the step of the method may be repeated.

In another aspect of the invention, dairy cows that are of suitable maturity and have been open a suitable period may be bred by a method wherein a first progesterone dose is administered to the cow. The cow is then inseminated nine days after administration of the first progesterone dose. A biological specimen is obtained from the cow at least seven and less than thirteen days after insemination. At least one assay is performed on the biological sample and a determination is made whether the cow is open based on the result from the assay. A second progesterone dose may be administered twelve days after insemination to a cow that is determined to be open and the cow may be inseminated nine days after the second progesterone dose. The progesterone doses may be administered by application of a vaginal insert and the vaginal inserts may be left in for seven days. Gonadotropin releasing hormone may be administered to the cow nine days before insemination. Prostaglandin F2α or cloprostentol may be administered to the cow two days before insemination.

In yet another aspect of the invention, dairy cattle may be bred by administering a first progesterone to a cow, administering a first gonadotropin releasing hormone dose to the cow on the same day, administering a second gonadotropin releasing hormone dose to the cow nine days after administration of the first gonadotropin releasing hormone dose, implanting an embryo into the cow seven days after the second gonadotropin releasing hormone dose, and administering a second progesterone dose to the cow twenty eight days after the first progesterone dose. Ultrasound may be performed on the cow thirty five days after the first progesterone dose and a determination made whether the cow is open based on the ultrasound. Where the cow is determined to be open, an embryo may be implanted into the open cow forty two days after the first progesterone dose. The first and second progesterone doses may be administered using a vaginal insert over a period of seven days. Prostaglandin F2α or cloprostenol may be administered to the cow seven days after the first progesterone dose.

DETAILED DESCRIPTION OF THE INVENTION

It has been shown by the inventor that the use of a progesterone insert nineteen days after artificial insemination service in female bovines, for example dairy cattle, along with early pregnancy detection (e.g. six to eight days after insertion or 25 to 27 days after AI service) can reduce the number of AI services required per conception, can decrease the number of days open and can allow the operator of a dairy operation to reduce the number of average days in milk in a herd. The early pregnancy detection may be performed using ultrasound imaging.

In another aspect of the invention, detection of pregnancy may be performed even sooner after AI service. Such detection may utilize methods for detection of biological markers of pregnancy, such as Early Conception Factor. Reagents for performing such detection methods are becoming increasingly available, allowing for detection in multiple animals on an economically acceptable basis. Of course, external factors such as weather, quantity and quality of feed rations, animal handling practices (including penning), facility and equipment management will also have a direct impact on the success of a breeding program using the method of the invention. Heat stress is widely known to decrease conception and full term pregnancy in dairy cattle.

Animal handling practice can have a substantial impact as well on breeding efforts. Cows need sure footing underneath. Penning practices are also important. To the extent possible, cows should be kept in the same groups to maintain stability of favorable social interactions unless other factors such as health concerns interfere. Efforts should also be made to keep cows in facilities where they are not in crowded conditions.

The invention can be more fully understood by reference to the following examples.

EXAMPLE 1

Cows are selected for breeding, typically at a point 50 days from birth (parturition). However, this voluntary waiting period may be 60, 70 or even 100 days after giving birth depending on management practices of a particular dairy operation. At Day 0 of the procedure, a progesterone insert is placed vaginally into the cow to be bred. The cow is also given 2 cc (~100 mcg) of gonadotropin releasing hormone (GnRH) as indicated by the manufacturer, typically by intramuscular (IM) injection. The progesterone insert may be an EAZI-BREED™ CIDR® cattle insert. The GnRH may be CYSTORELIN® GNRH available from Merial Limited, Duluth, Ga. On Day 7, the progesterone insert is removed and 25 mg of dinoprost (prostaglandin F2α) is administered as indicated by the manufacturer, typically by IM injection. The dinoprost may be obtained under the LUTALYZE® brand name from Pfizer Animal Health Products as a dinoprost tromethamine sterile solution.

At Day 9, the cow undergoes artificial insemination (AI) service using standard methods and 75 mcg GnRH is administered. On Day 28 (19 days post breeding), a progesterone insert is again administered vaginally and 100 mcg of GNRH is administered to the cow by IM injection. At Day 35 (26 days post breeding) the progesterone insert is removed and the cow is checked by ultrasound to determine whether or not the cow is open. Open cows are returned to the treatment cycle described at Day 7. Cows identified as pregnant may then be treated at Day 42 (33 days post breeding) with a progesterone insert again administered vaginally. In addition, 100 mcg of GnRH may be administered to the cow by IM injection. Alternatively, if personnel and equipment are available at Day 42, a pregnancy check may be carried out by ultrasound. If the cow is pregnant, the animal is no longer treated with additional hormone therapy and the pregnancy is allowed to continue to term. At Day 49 (40 days post breeding), the progesterone insert is removed and the cow is checked by ultrasound to verify pregnancy. Open cows are returned to Day 7 of the protocol. Finally, pregnancy is again confirmed by ultrasound at Day 70 (61 days post breeding.)

Variations of this method will be obvious to those skilled in the art. However, the most important step in this method is the introduction of exogenous progesterone into the cow at Day 19. This step, combined with the early pregnancy check at Day 26, allows for rapid reentry into an AI servicing schedule thereby reducing days open for all cows being treated with this method. Without being limited by any particular theory, it is believed that the reintroduction of progesterone during the early stages of pregnancy may increase survival rates for these pregnancies.

EXAMPLE 2

Cows are selected for breeding, typically at a point 50 days from birth (parturition). However, this voluntary waiting period may be 60, 70 or even 100 days after giving birth depending on management practices of a particular dairy operation. At Day 0 of the procedure, a progesterone insert is placed vaginally into the cow to be bred. The cow is also given 2 cc (~100 mcg) of gonadotropin releasing hormone (GnRH) as indicated by the manufacturer, typically by intramuscular (IM) injection. The progesterone insert may be an EAZI-BREED™ CIDR® cattle insert. On Day 7, the progesterone insert is removed and 2 cc (25 µg) of cloprostentol (structurally related prostaglandin F2α) is administered as indicated by the manufacturer, typically by IM injection or subcutaneous injection in the anterior half of the neck. The cloprostentol may be obtained under the ESTRUMATE® brand name from Schering-Plough Animal Health Ltd. Wellington, New Zealand. At Day 9, the cow receives artificial insemination (AI) service using standard methods and 100 µg GnRH (e.g. CYSTORELIN) is administered. On Day 16 biological samples (e.g. blood or first strip milk samples) are taken for each cow impregnated at Day 9 and the samples are then evaluated using one or more assays to determine whether the cow is open. The assay may be performed using an EDP/ECF™ early conception factor test. This test is available from EDP Biotech Corporation, Knoxville, Tenn. Alternatively, the EDP/ECF™ early conception factor test could be administered anytime between Day 16 and Day 21. On Day 21, all cows identified as open receive a progesterone insert, 100 µg GnRH and are returned to Day 0 of the protocol.

On Day 28 (19 days post AI), a progesterone insert is again administered vaginally and 100 mcg of GnRH is administered to the cow. At Day 35 (26 days post AI) and the cow is checked by ultrasound to determine whether or not the cow is open. Open cows have the progesterone insert removed are returned to the treatment cycle described at Day 7. The progesterone insert is left in the cows that are pregnant. Again at Day 42 (33 days post AI) a pregnancy test is again performed on the cows that were pregnant on Day 26. The progesterone insert is removed from all cows. If a cow is open, 2 cc of ESTRUMATE prostaglandin is administered and the cow is returned to Day 7 of the protocol. At Day 63 (54 days post AI), another pregnancy check is administered. Open cows are returned to Day 0 of the protocol. By use of the EDP/ECF™ test at Day 16 to identify open cows and the return of those open cows to Day 0 of the protocol, the cows are bred more efficiently and the number of days open should be fewer. Again, the AI service on Day 9 is done in the absence of heat detection, behavioral or otherwise.

EXAMPLE 3

Another aspect of the invention is the facilitation the transfer of large groups of timed embryo transfers to recipient cows on dairy farms without relying on the expression of heats or heat detection.

The transfer of viable embryos (such as 7-day embryos) into recipient females allows for the recipient cow the opportunity to become pregnant regardless of the quality of her own oocytes. For example, cows under metabolic stress due to overcrowding, comfort issues, weather stress, nutritional stress and post-partum difficulties tend to produce lower quality oocytes which as a result have a lower viability both as fertilizable oocytes and as developing embryos. By placing a higher quality embryo in these cows, the chances for a successful pregnancy are believed to be improved and as a result, overall herd reproductive parameters would likewise also be improved. Furthermore, this system allows for the large scale introduction of new genetics into a herd and can be used with programs that produce large numbers of same or similar genetics sex-selected (e.g. female) embryos to increase the number and quality of replacements in a herd.

At Day 0 of the procedure, a progesterone insert is placed vaginally into the cow to be bred. The cow is also given gonadotropin releasing hormone (GnRH) (e.g. 2 cc (~100 mcg)) as indicated by the manufacturer, typically by intramuscular (IM) injection. The progesterone insert may be an EAZI-BREED™ CIDR® cattle insert. The GnRH may be CYSTORELIN® GnRH available from Merial Limited, Duluth, Ga. On Day 7, the progesterone insert is removed and 25 mg of dinoprost (prostaglandin F2α) or cloprostenol (structurally related prostaglandin F2α) is administered as indicated by the manufacturer, typically by IM injection. The dinoprost may be obtained under the LUTALYZE® brand name from Pfizer Animal Health Products as a dinoprost tromethamine sterile solution. On Day 9, GnRH (e.g. 75 mcg) is administered is administered to the cow. On Day 16, embryo transfer is performed. The transfer may be accomplished using standard procedures for such transfers.

On Day 28, a progesterone insert is administered to the cow. The cow is also given gonadotropin releasing hormone (e.g. 2 cc (~100 mcg)) as described above. On Day 35, the progesterone insert is removed and a pregnancy check is performed using ultrasound. Cows that are determined to be open are returned to Day 7 of the protocol. Cows that are determined to be pregnant are rechecked for pregnancy seven days later (i.e. Day 42). Cows that are determined to be open at Day 42 are returned to Day 0 of the protocol. Cows that are determined to be pregnant are rechecked for pregnancy twenty days later (i.e. Day 63). Cows that are determined to be open at Day 63 are returned to Day 0 of the protocol.

While certain numbers of days for accomplishing certain steps are specified herein, one skilled in the art will recognize that deviation slightly from the exact numbers will be possible. Many of the numbers, however, are specified to allow for regular weekly treatment of herds. This regular treatment may allow for convenient scheduling of professional services, especially veterinary service. Therefore, it will be appreciated that various changes can be made therein without departing from the spirit and scope of the invention.

The invention claimed is:

1. A method for breeding dairy cattle that increases breeding efficiency with a reduction in the number of months in the breeding cycle without the need for detecting standing estrus of a dairy cow prior to insemination, the method comprising the steps of:
    administering a first progesterone dose to a cow;
    inseminating the cow nine days after administering progesterone;
    administering a second progesterone dose to the cow nineteen days after insemination;
    performing ultrasound on the cow twenty six days after insemination; and
    determining whether or not the cow is pregnant.

2. The method of claim 1, further comprising the step of administering gonadotropin releasing hormone to the cow nineteen days after insemination.

3. The method of claim 1, wherein the first progesterone dose is administered by application of a first vaginal insert and the second progesterone dose is administered by application of a second vaginal insert.

4. The method of claim 3, wherein the first vaginal insert is removed two days before insemination and the second vaginal insert is removed twenty six days after insemination.

5. The method of claim 4, further comprising the step of administering gonadotropin releasing hormone to the cow nine days before insemination.

6. The method of claim 5, further comprising the step of administering prostaglandin F2α or cloprostenol to the cow two days before insemination.

7. The method of claim 1, wherein if the cow is determined not to be pregnant the method further comprising the steps of
    inseminating the cow two days after the cow is determined not to be pregnant;
    administering a third progesterone dose to the cow nineteen days after the second insemination;
    performing ultrasound on the cow twenty six days after the second insemination; and
    determining whether or not the cow is pregnant.

8. A method for breeding dairy cattle that increases breeding efficiency with a reduction in the number of months in the breeding cycle without the need for detecting standing estrus of a dairy cow prior to insemination, the method comprising the steps of:
    administering a first progesterone dose to a cow;
    inseminating the cow nine days after administration of the first progesterone dose;
    obtaining a biological specimen from the cow between seven and twelve days after insemination;
    performing at least one assay on the biological sample;
    determining whether or not the cow is pregnant based on the result from the assay; and
    administering a second progesterone dose, wherein the second progesterone dose is administered nineteen days after insemination if it is determined based on the result from the assay that the cow is pregnant, and wherein the second progesterone does is administered twelve days after insemination if it is determined based on the result from the assay that the cow is not pregnant.

9. The method of claim 8, further comprising the step of:
    inseminating the cow nine days after the second progesterone dose if it is determined based on the result from the assay that the cow is not pregnant.

10. The method of claim 8, wherein the first progesterone dose is administered by application of a vaginal insert.

11. The method of claim 10, wherein the insert is removed two days before insemination.

12. The method of claim 8, further comprising the step of administering gonadotropin releasing hormone to the cow nine days before insemination.

13. The method of claim 8, further comprising the step of administering prostaglandin F2α or cloprostentol to the cow two days before insemination.

14. A method for breeding dairy cattle that increases breeding efficiency with a reduction in the number of months in the breeding cycle without the need for detecting standing estrus of a dairy cow prior to embryo implantation, the method comprising the steps of:
   administering a first progesterone to a cow;
   administering a first gonadotropin releasing hormone dose to the cow on the same day;
   administering a second gonadotropin releasing hormone dose to the cow nine days after administration of the first gonadotropin releasing hormone dose;
   implanting an embryo into the cow seven days after the second gonadotropin releasing hormone dose; and
   administering a second progesterone dose to the cow twelve days after embryo implantation.

15. The method of claim 14, further comprising the steps of:
   performing ultrasound on the cow thirty five days after the first progesterone dose; and
   determining whether or not the cow is pregnant.

16. The method of claim 15, further comprising implanting an embryo into the cow that is not pregnant forty two days after the first progesterone dose.

17. The method of claim 14, wherein the first and second progesterone doses are administered using a vaginal insert.

18. The method of claim 17, further comprising the steps of removing the vaginal insert used to administer the first dose seven days after administration of the vaginal insert, and removing the vaginal insert used to administer the second dose seven days after administration of the vaginal insert.

19. The method of claim 14, further comprising the step of administering prostaglandin F2α or cloprostentol to the cow seven days after the first progesterone dose.

* * * * *